United States Patent [19]

Woerly

[11] Patent Number: 5,863,551
[45] Date of Patent: Jan. 26, 1999

[54] IMPLANTABLE POLYMER HYDROGEL FOR THERAPEUTIC USES

[75] Inventor: Stéphane Woerly, Québec, Canada

[73] Assignee: Organogel Canada LTEE, Sainte-Foy, Canada

[21] Appl. No.: 731,484

[22] Filed: Oct. 16, 1996

[51] Int. Cl.$^6$ .......................... A61K 31/785; A61K 47/32; A61L 31/00
[52] U.S. Cl. ........................ 424/423; 424/78.08; 424/487; 526/199; 526/200; 623/11; 523/113
[58] Field of Search ................................. 424/78.08, 423; 526/199, 200

[56] References Cited

U.S. PATENT DOCUMENTS 4,902,295  2/1990  Walthall et al. .

OTHER PUBLICATIONS

Xu et al. J. Comp. Neurol. 351, 145, 1995.
Woerly et al. Biomaterials, 11, 97, 1990.
Woerly et al. Biomaterials, 12, 197, 1991.
Woerly et al. J. Neural Transpl. Plast 3, 21, 1992.
Woerly et al. Cell Transpl., 2, 229, 1993.
Woerly et al. J. Neural Transpl. Plast., 5, 245, 1995.
Harvey et al. Brain Res., 671,119,1995.
Bellamkonda et al. *Hydrogel–based 3–dimensional matrix for neural cells*, J. Biomed Mat. Res. 29, 663–671, 1995.
Krewson et al. *Cell aggregatyion and neurite growth in gels of extracellular matrix molecules*, Biotechnol. Bioeng. 43, 555–562, 1994.
Wald et al. *Cell seeding in porous transplantation*, Biomat. 14, 270–278,1993.
Woerly et al. Neurosci. Lett. 205, 197–201, 1996.

*Primary Examiner*—Peter F. Kulkosky
*Attorney, Agent, or Firm*—Oblon, Spivak, McClelland, Maier & Neustadt, P.C.

[57] ABSTRACT

The hydrogel is a copolymer of an N-substituted methacrylamide or acrylamide, a cross-linking agent and a complex sugar or derivative, a tissue adhesion peptide or a polymer conjugate with antibodies, the polymer being heterogeneous, elastically deformable and having an equilibrium water content of at least about 80%. It can be used for tissue regeneration and for organ repair, for example, in the developing and adult nervous system.

14 Claims, 1 Drawing Sheet

IMPLANTABLE POLYMER HYDROGEL FOR THERAPEUTIC USES

TECHNICAL FIELD (a) Field of the Invention

This invention relates to a polymer hydrogel. More particularly, the present invention is concerned with a porous, implantable polymer hydrogel for therapeutic uses, for example, which can be used for internal tissue replacement of any portion of soft organs, for wound healing, for tissue regeneration, and for organ repair in general, especially in the developing and adult nervous system, and other like therapies. The invention is especially directed at a polymer hydrogel which, upon implantation becomes a porous matrix which is filled with biological fluids and molecules to form a so-called organoid hydrogel, and becomes progressively integrated into the host by subsequent ingrowth of tissue and blood vessels. The invention also relates to a method of introducing living tissue cells, precursor cells or genetically modified cells within such polymer hydrogel to produce biohybrid materials which are useful for three-dimensional cell cultures or for tissue reconstruction. The invention also relates to a method for the production of the polymer hydrogel according to the invention, and to biohybrid materials produced by the method mentioned above. Finally, the present invention relates to a method for treating damaged parts of the central nervous system, especially the spinal cord and optic nerve, or of peripheral nerves, or other tissues by implantation therein of the polymer hydrogel or the biohydrid materials according to the invention.

BACKGROUND ART (b) Description of Prior Art

Organ transplantation is presently the only alternative to alleviate organ failures and to restore or improve the function and performance of organs. However, some of the drawbacks of organ-transplant therapies, are the potential for donor-to-recipients disease transmission, the shortage and the limited availability of donor organs, and possible immunological cross-reactions.

Thus, for example, spinal cord transplantation is neither clinically nor biologically feasible and consequently there is no treatment available for SCI patients, while in the United States alone there are 250,000 chronically paralyzed patients with an increase of 10,000 new SCI patients each year.

On the other hand, implantation, transplantation or injection of cells into the body to replace or restore missing cells or part of tissue organs cannot properly achieve formation of new tissues because of the lack of a supporting extracellular matrix as a necessary tissue framework for tissue expansion and organization into an integrated structure in contact with the host organ. In addition, the cells need to be placed in a physiologically-equivalent environment that facilitate diffusion of nutrients, oxygen, humoral and cellular components in order to maintain high cell viability and growth potential after implantation.

Porous hydrogels of the present invention are deformable porous polymer matrices saturated with interstitial fluid or water, and thus provide the necessary tissue framework and hydrated space through which the cells can proliferate and assemble into supracellular tissue architectures in a correct histological structure to obtain a functional neotissue.

Different experimental strategies of intraspinal transplantation have been disclosed in the literature as attempts to restore damages in the spinal cord (animal models), using various implant materials which can be grouped into two broad categories of implants: (1) biological tissues and (2) prosthetic materials.

In category (1) is included the use of donor tissue grafts, either syngenic autograft or homograft, allograft or xenograft, to bridge lesions of spinal cord such as fetal neural tissue, either as (a) a solid graft (e.g. Bregman, Dev. Brain Res., 34, 265, 1987; Houlé and Reier, J. Comp. Neurol., 269, 535, 1988) or as (b) suspension grafts including mixed neural tissue cells (e.g. Goldberg and Bernstein, J. Neuroscience Res., 19, 34, 1988; Hoovler and Wrathall, Acta Neuropathol., 81, 303, 1991); Schwann cells recombined with cultured sensory neurons (Kuhlengel et al., J. Comp. Neurol., 293, 74, 1990); immature astrocytes (e.g., Bernstein and Goldberg, Res. Neurol. Neurosci., 2, 261, 1991); precursors of neural tissue cells (Monteros et al., Dev. Neurosci., 14, 98, 1992) and immortalized established cell lines (Zompa et al., Int. J. Dev. Neurosci., 11, 535, 1993); peripheral nerve segment including cultured non-neuronal cells (Wrathall et al, Acta Neuropathol., 57, 59, 1982) or with embryonic neural tissue (Horvat et al., Res. Neurol. Neurosci., 2, 289, 1991). For category (2) prosthetic materials which have been disclosed include pure collagen matrices (de la Torre and Goldsmith, Brain Res., Bull., 35, 418, 1994; Marchand and Woerly, Neurosci. 36, 45, 1990; Gelderg, Brain Res. 511, 80, 1990), containing neuroactive agents (Goldsmith and de la Torre, Brain Res., 589, 217, 1992) or including cultured neural grafts (Bernstein and Goldberg, Brain Res. 377, 403, 1986); treated nitrocellulose implants (Schreyer and Jones, Dev. Brain Res., 35, 291, 1987; Houlé and Johnson, Neurosci. Lett. 103, 17, 1989); collagen implants (Paino et al., J. Neurocytol., 23, 433, 1991) and polymer guidance channels of poly(acrylonitrile-vinyl chloride) (Xu et al., J. Comp. Neurol., 351, 145, 1995) enclosing Schwann cells.

These approaches focus very sharply on the promotion of axonal regeneration using various tissue substrates as sources of new axons or using complex prosthetic substrates to support and guide growing axons, and do not address the clinically relevant issue of spinal cord or brain tissue repair by regeneration of the bulk of the host tissue and remodeling of wound healing, for example, after removing necrotic or scar tissue following injury.

Polymer hydrogels have been disclosed as implants in the nervous system (Woerly et al., Biomaterials, 11, 97, 1990; Woerly et al., Biomaterials, 12, 197, 1991; Woerly et al., J. Neural Transpl. Plast. 3, 21, 1992; Woerly et al., Cell Transpl., 2, 229, 1993; Woerly et al., J. Neural Transpl. Plast., 5, 245, 1995). These hydrogels were prepared by free radical polymerization in water, using ammonium persulfate and sodium metabisulfite or persulfate and ascorbic acid as redox initiators with either hydroxyethyl methacrylate (pHEMA), glycidyl methacrylate pGMA) or N-hydroxypropyl methacrylamide (pHPMA) or a composition including the above monomers with a cross-linking agent which is either ethylene glycol and tetraethylene glycol dimethacrylate or methylene-bis-acrylamide. These gels are typically homogeneous and optically transparent with a bimodal porosity including open (accessible pore volume) and closed pores as shown by mercury porosimetry data and scanning electron microscopy; typically the porous structure for these gels is formed of parallel cylindrical capillaries of circular cross-section as shown in FIG. 1 with an average pore diameter of 7 to 13 $\mu$m. The fractional porosity is in the range of 50% to 85% for pHEMA hydrogels, 60% to 65% for pGMA hydrogels and 70% to 94% for pHPMA hydrogels. At least 50% of the porous volume of the hydrogel is occupied by pore from 1.2 to 4 $\mu$m for pHEMA, 6 to 13 $\mu$m for pGMA and 10 to 14 $\mu$m for pHPMA. It was found that their biological activity was dependent upon the introduction or copolymerization of collagen into the cross-linked network. Applicant experimented implantation in the brain which showed that some degree of tissue repair can be achieved according to the degree of tissue ingrowth into the homogeneous gel matrices. This reaction is variable according to the monomer composition and added functional groups. However, homogeneous hydrogels frequently induce the formation of fibrous capsule that tend to isolate the implant from the host. This is due to the mechanical properties of these gels that do not match sufficiently those of the living neural tissue as well as to the small volume fraction of macropores. In the spinal cord, these homogeneous hydrogels do not integrate into the host and become rapidly encapsulated by a connective tissue and glial scar without penetration of axons or tissue components, as shown in FIG. 2. In addition, there is a physical consideration that limits the surface area that can be generated, an important parameter for successful tissue interaction generated by the cylindrical pores in such homogeneous gels. For a fixed volume of gel, the surface area reaches a limit which is the maximum radius of a single pore occupying the total volume of the gel. On the other hand, increasing the surface area by decreasing the size of pores will lead to a decrease of the total void volume which is incompatible with tissue ingrowth and biomass accumulation.

Harvey et al., in Brain Res., 671, 119, 1995 discloses a polymer sponge of poly(2-hydroxyethyl methacrylate) that is used as brain implant for tissue regeneration and axon growth. This product is best used with the addition of collagen to the polymer network as tissue bioadhesive and after inclusion of Schwann cells.

U.S. Pat. No. 4,902,295 describes a process for preparing an artificial tissue from pancreas tissue cells. The process involves the polymerization of matrix precursors, gel precursors and promoters with viable cells in aqueous phase. All polymer precursors as well as promotors are biological compounds susceptible of rapid biodegration into the body and do not have long term stability after implantation.

Bellamkonda, R.; Ranieri, J. P.; Bouche, N.; Aebischer, P. ("Hydrogel-Based Three-dimensional Matrix for Neural Cells", J. Biomed. Mat. Res. 1995, 29, 663–671) describe a technique to immobilize neural tissue cells into agarose and extracellular-equivalent (Matrigel®) gels. These materials are biologic and are biodegradable.

Krewson, C. E.; Chung, S. W.; Dai, W.; Saltzman, W. M. ("Cell Aggregation and Neurite Growth in Gels of Extracellular Matrix Molecules". Biotechnol. Bioeng. 1994, 43, 555–562) describe a technique where PC12 cells are suspended in gels of collagen alone or combined with fibronectin or laminin, and in gels of agarose and collagen. These gels are biodegradable.

Cascone, M. G.; Laus, M.; Ricci, D.; Sbarbati del Guerra, R. ("Evaluation of Poly(vinyl alcohol) Hydrogels as a Component of Hybrid Artificial Tissues", J. Mat. Sci. Mat. Med. 1995, 6, 71–75) describe a technology using poly (vinyl alcohol) hydrogels, physically cross-linked, into which fibroblastic cells are introduced by a one freeze-thawing cycle.

Wald, H. L.; Sarakinos, G.; Lyman, M. D.; Mikos, A. G.; Vacanti, J. P.; Langer, R. ("Cell Seeding in Porous Transplantation", Biomat. 1993, 14, 270–278) describe a process for enclosing hepatocyte cells into degradable polymer foams of poly(L-lactic acid) by a microinjection technique. This technique does not provide a non-degradable matrix and does not allow uniform cell distribution throughout the polymer matrix.

Mikos, A. G.; Bao, Y.; Cima, L. G.; Ingber, D. E.; Vacanti, J. P.; Langer, R. ("Preparation of Poly(glycolic acid) Bonded Fiber Structures for Cell Attachment and Transplantation", J. Biomed. Mat. Res. 1993, 27 183–189) describe a process to build networks of poly(glycolic acid) with bonded fibers to culture hepatocytes. This polymer is biodegradable and the process to introduce cells into the matrix is different from entrapment.

Puerlacher, W. C.; Mooney, D.; Langer, R.; Upton, J.; Vacanti, J. P.; Vacanti, C. A. ("Design of Nasoseptal Cartilage Replacements Synthetized from Biodegradable Polymers and Chondrocytes", Biomat. 1994, 15, 774–778) and Freed, L. E.; Marquis, J. C.; Nohria, A. Emmanual; Mikos, A. G.; Langer, R. ("Neocartilage Formation In Vitro and In Vivo Using Cells Cultured on Synthetic Biodegradable Polymers", J. Biomed. Mat. Res. 1993 27, 11–23). These references describe a process to introduce chondrocyte cells into polyglycolic (PGA) or polylactic acid (PLLA) or PGA-PLLA matrices by capillary action. This process yields biodegradable polymer materials while the cells are not uniformly distributed into the polymer and does not allow to control cell density.

Cao, Y.; Vacanti, J. P.; Ma, X.; Paige; K. T.; Upton, J.; Chowanski, Z.; Schloo, B.; Langer, R.; Vacanti, C. A. ("Generation of Neo-Tendon Using Synthetic Polymers Seeded with Tenocytes", Transpl. Proc 1994, 26, 3390–3391) describe a process to seed tenocyte cells into embossed nonwoven mesh of polyglycolic acid.

Mooney, D. J.; Park, S.; Kaufman, P. M.; Sano, K.; McNamara, K.; Vacanti, J. P.; Langer, R. ("Biodegradable Sponge for Hepatocyte Transplantation", J. Biomed. Mat. Res 1995, 29, 959–965) and Takeda, T.; Kim, T. H.; Lee, S. K.; Langer, R.; Vacanti, J. O. ("Hepatocyle Transplantation in Biodegradable Polymer Scaffolds Using the Baltimatian Dog model of Hyperuricosuria", Transpl. Proc. 1995, 27, 635–636) describe a process to absorb hepatocyte cells in sheets of polyglycolic acid polymer felts or into polymer sponges fabricated from polylactic acid and polyvinyl alcohol and from polylactic acid glycolic acid by adsorption and capillary action. This process yields biodegradable polymer materials while the cells are not uniformly distributed into the polymer and does not allow to control cell density.

Woerly, S.; Plant, G. W.; Harvey, A. R. ("Cultured Rat Neuronal and Glial Cells Entrapped within Hydrogel Polymer Matrices: A Potential Tool for Neural Tissue Replacement", Neurosci. Lett. 1996, 205, 197–201) disclose a procedure to entrap neural tissue cells into homogeneous transparent polymer gels of poly[N-(2-hydroxypropyl)-methacrylamide] which can contain collagen as attachment substrate. This procedure involves the addition of a cell suspension to the polymer mixture and the polymerization of the cell-polymer mixture at room temperature or in an incubator maintained at 37° C. The resulting gel is optically transparent and cells are randomly dispersed within the cross-linked gel. Immunocytochemical studies indicated that cell viability after 6 days in vitro varied between 0 and 6%.

SUMMARY OF INVENTION

Figure 1:
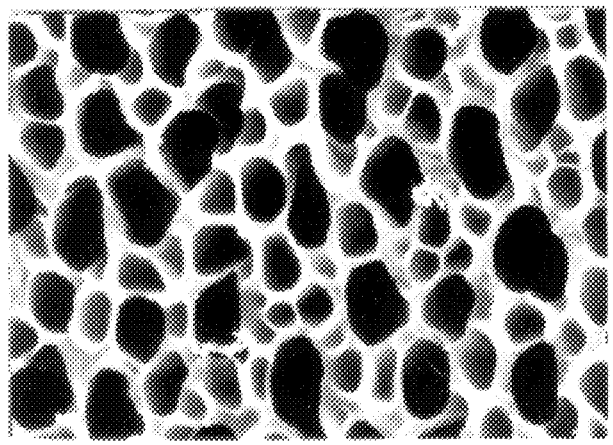
FIG. 1 is a microscopical view of a homogeneous gel.
Figure 2:
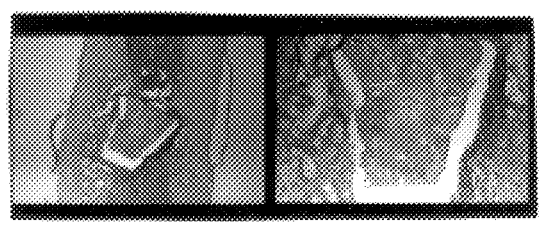
FIG. 2 is a microscopical view of a homogeneous gel implanted in spinal cirdl

It is an object of the present invention to prevent the drawbacks of the prior art by using a non-biological prosthetic device such as a non-degradable polymer hydrogel, that acts as space-filling material and as scaffold builders that stimulate tissue regeneration, morphogenesis and remodeling into an integrated structure-to-organ.

It is another object of the present invention to improve the healing of tissue into tissue formation that can be achieved by controlling cell proliferation, cell infiltration and tissue organization within a stable polymer matrix.

It is another object of the present invention to provide for tissue regeneration by means of polymer matrices which would have a great benefit and an important clinical and economical impact for people suffering from spinal cord (SCI) and brain injuries or developmentally defective spinal cord (spina bifida).

It is another object of the invention to provide polymer matrices for regeneration of the optic nerve and peripheral nerves.

It is another object of the present invention to provide a non-degradable synthetic polymer hydrogel matrix with anisotropic porous structure, effective surface area and good tissue adhesivity and compatibility and which is designed for implantation in soft tissue structure, especially in the nervous system, and which becomes progressively part of the organ.

It is another object of the present invention to provide for the therapeutic use of synthetic polymer matrices with controlled pore structure and carrying surface active agents.

It is a primary object of the present invention to provide a polymer matrix which is made of a novel water-insoluble polymer hydrogel that is used in the swollen state as prosthetic devices for tissue regeneration for soft organ repair.

It is another object of the invention to provide a method for the production of a hydrogel product in a mold having the shape of the final prosthetic device.

It is yet another object of the present invention to overcome one or more drawbacks of the prior art and to provide a polymer neuroprosthesis which can be implanted in the brain or spinal cord using standard surgical procedures.

It is a further object of this invention to provide a method by which cells or genetically modified cells can be introduced into polymer networks.

It is another object of the present invention to provide a polymer mixture that can be mixed with living cells, thereby combining the physical characteristics of a polymer matrix with hydrogel-type behavior (porosity, stability, guidance surfaces, permeability) and with cellular biological factors (e.g., growth factors).

Still another object of this invention is to provide biohybrid devices which can be used to replace part of tissue of soft organs.

Yet still another object of the present invention is to provide a three-dimensional culture system which can be used to culture a variety of cells in vitro for a prolonged period of time.

Another object of the invention is to provide support matrices for the attachment of biologically-active molecules to tissue or organs.

It is another object of the present invention to provide porous hydrogels which are deformable porous polymer matrices saturated with interstitial fluid or water, thereby providing the necessary tissue framework and hydrated space through which the cells can proliferate and assemble into supercellular architectures in a correct histological structure to give a functional tissue.

Another object of the present invention is to provide a component for systems for controlled release of drugs and macro-molecules, especially anti-inflamatory substances such as indomethacin, stimulators of cytokins, such as bacterial lipopolysaccharides, steroids, such as methyl prednisolone and neuroactive factors, such as fibroblast growth factors.

It is another object of the invention to provide a material which possesses strong bio-adhesiveness and hemostatic properties suitable for internal soft tissue placement, rapid attachment and at the same time hemostasis.

It is a primary object of the present invention to provide a polymer matrix which has mechanical and chemical stability to sustain long term implantation in the body without degradation that could otherwise damage the new tissue networks that has grown into the matrix in replacement of a part of an organ.

It is also another object of the present invention to provide a matrix with the mechanical compliance that allow to cut, to size and to handle the polymer matrix by the operator without changing the internal structure and the mechanical properties of the matrix.

Another object of the present invention is to provide a swellable material with a high swelling capacity in aqueous media that can adsorb significant amounts of biological interest for the purpose of the present invention such as adhesion molecules, such as CAM and L1 molecules, or guidance molecules such as semaphorins or netrins dissolved in a suitable solution, so that the said molecules are subsequently adsorbed onto the surface of the network of the polymer matrix.

According to the invention there are provided new hydrophilic polymeric hydrogels which are capable of forming porous, soft, highly absorbent polymer matrices which are elastically deformable and possess an equilibrium water content of at least about 80%, preferably at least 96%.

There is also provided, according to the invention, polymer mixtures which can be mixed with living cells.

The invention relates to a polymer hydrogel for therapeutic use, which is a copolymer of (a) an N-substituted methacrylamide or acrylamide, (b) a cross-linking agent, and (c) a polymerizable material selected from the group consisting of a sugar, a sugar derivative, a tissue adhesion peptide, and a polymer conjugate with antibodies against lipid derivatives, which is elastically deformable and possesses an equilibrium water content of at least about 80%, preferably at least 96%.

Preferably, the N-substituted methacrylamide or acrylamide (a) is selected from the group consisting of N-monoalkyl and N,N-dialkyl methacrylamides and acrylamides, the cross-linking agent, (b) comprises acrylamide or precursors thereof and the polymerizable material, (c) is a sugar which is selected from the group consisting of glucosamine, N-acetyl glucosamine and an N-acetyl derivative of neuraminic acid and their polymeric forms such as polysialic acid.

The invention also relates to a method for preparing a polymer hydrogel for therapeutic use which comprises (a)

dissolving a cross-linking agent in a pore-forming solvent with a free radical polymerization initiator to form a solution, (b) adding an N-substituted methacrylamide or acrylamide to the solution obtained in (a) to form a mixture, and (c) adding a solution of a sugar, a sugar derivative, a tissue adhesion peptide or a polymer conjugate with antibodies against lipid derivatives to the mixture obtained in (b).

In accordance with a preferred embodiment, the method comprises dissolving azo-bisisobutyronitrile and methylene bisacrylamide in the solvent to form a solution, mixing the solution with N-2-(hydroxypropyl) methacrylamide, adding glucosamine or N-acetylglucosamine or N-acetylneuraminic acid thereto, and removing low molecular weight residual products and initiator traces therefrom.

In accordance with another embodiment, the method also comprises adding living tissue cells or genetically modified cells to the product obtained in (c) and effecting polymerization of the cells within said product.

According to yet another embodiment, the polymer hydrogel according to the invention comprises cells or genetically modified cells polymerized therewith.

According to yet another embodiment, the invention relates to a method for treating damaged cerebral tissues or spinal cord injuries which comprises removing the damaged cerebral tissues or spinal cord in a human being or animal and replacing the damaged cerebral tissues or spinal cord with a polymer hydrogel according to the invention.

The hydrogel according to the invention is a covalently cross-linked, non-transparent, heterogeneous material, which preferably shows a clear phase separated structure formed of polymer particles of about 1 to 10, preferably 3 to 5 $\mu$m so as to provide an area of relatively coarse porosity (macropores) where the hydrogel is intended to interface with a host tissue and relatively fine porosity (mesopores) where it is intended to interface with ingrowing tissue.

This results in a preferably sponge-like structure with a macroporous structure; a fractional porosity of, for example, at least 80 to 90% (volume of mercury intrusion to the total volume of gel); a specific surface area in the range of preferably hundreds of square meter/gram of gel; a median pore diameter (volume), of for example, about 15 to 35 $\mu$m; a porous volume for pores equal to or greater than 10 $\mu$m equal to 100% of the fractional porosity of the hydrogel; a hyperporous character (fractional porosity of the gel at least 50% of the gel volume) from 20–30 $\mu$m.

The macrostructure and porosity of the hydrogels can be manipulated by controlling the size of the particles and the porous structure which depend on the composition and the properties of the pore-forming solvent used, the polymer volume fraction, the polymer-solvent interaction, the polymerization temperature and the properties of the cross-linking monomer used. Successful biomass accumulation and cell interaction result from such an optimal surface/ volume interaction as shown by mercury porosimetry data that result from micro- and mesoporosity of the polymer particles.

Figure 3:
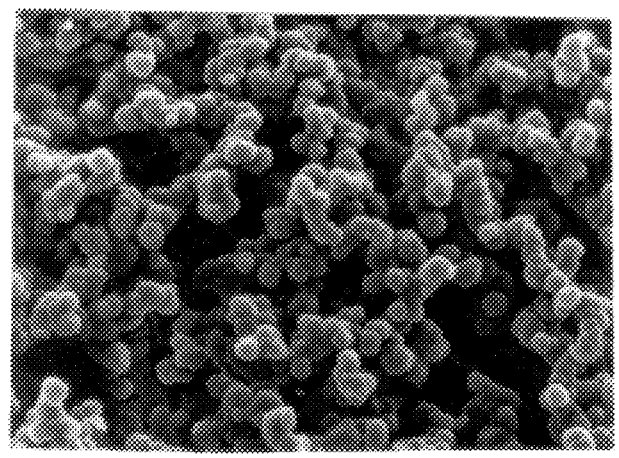
FIG. 3 is a microscopical view of a heterogeneous gel of HPMA.

An important final aspect of the material is its open nature and interconnectedness suitable for biomass cell accumulation and cell/molecular interactions with live tissue. Under scanning electron microscopy, as shown in FIG. 3, these heterogeneous gels typically show a colloidal-type three-dimensional structure with a non-circular pore and the wall of the pore system which is represented by the contiguity of the surface of polymer aggregates, as shown in the drawings. The effective surface area is a function of the porosity of the particle surface. In contrast to homogeneous gels, a major advantage of such heterogeneous gels is that the surface area generated by particles is virtually unlimited as the size of the aggregates (1) decreases so that the surface area is inversely proportional to 1. Also, as compared to homogeneous hydrogels, the heterogeneous hydrogels of the present invention show a much larger porous microprobe volume and therefore are more effective for cell infiltration and biomass accumulation. In addition and as compared to homogeneous hydrogels, the hydrogels according to the invention have mechanical compliance properties matching those of adult and developing neural tissue.

These hydrogel matrices have true tissue-specific architectures because cell interaction results in an organized tissue network through the gel structures, so-called organoid hydrogels.

The polymer matrices may be formed by simultaneous precipitation or precipitate polymerization and cross-linking copolymerization of an effective amount of each of the following components: (i) N-substituted methacrylamides such as N-monoalkylmethacrylamides or N-substituted acrylamides such as N-monoalkylacrylamides, or N,N-disubstituted acrylamides, such as N,N-dialkylacrylamides; (ii) a cross-linking agent, such as acrylamide or precursors thereof or divinyl compounds, and the like; (iii) a free radical polymerization initiator, such as azobisisobutyronitrile, various peroxides, ascorbic acid, peroxysulfates, substituted azo compounds and the like which are well known to those skilled in the art, in amounts which may vary between 0.01 to 2% by weight with respect to the copolymer or terpolymer; (iv) complex sugars such as glucosamine or N-acetylglucosamine or N-acetylgalactosamine or N-acetylneuraminic acid or poly-sialic acid or other sugar derivatives or tissue adhesion oligopeptides containing sequences, such as Arg-Gly-Asp, Ile-Lys-Val-Ala-Val, Ala His-Ala-Val-Ser-Glu, Tyr-Ile-Gly-Ser-Arg or polymer conjugate with antibodies against myelin and axon-associated lipids and their derivatives in a solvent preferably acetone/dimethyl sulfoxide, acetone or acetone/ethanol.

The alkyl groups preferably have one to two carbon atoms, for example $C_1$ to $C_2$ hydroxyalkyl and amino alkyl radicals. The term N-substituted as used herein includes $C_{1-8}$ substituents which may contain OH, an amino group or a combination thereof.

The reaction is generally carried out at a temperature of 40° to 60° C. in polymerization vessels consisting of sealed ampoules for a period of about 12 hours.

The invention is illustrated by means of the following Example.

EXAMPLE 1

AIBN (azobisisobutyronitrile) (1.2% w/w) and methylenebisacrylamide (1 mol%) are dissolved in dry acetone. The solution is mixed with N-2-(hydroxypropyl) methacrylamide to a volume ratio of 30% HPMA with a mixture of acetone/dimethylsulfoxide (93:7 v/v). A monomeric sugar, in this case glucosamine, is dissolved in dimethylsulfoxide and added to the polymerization mixture. The mixture is thoroughly homogenized and loaded in a syringe and injected in ampoules. The reaction mixture is then purged with nitrogen and the ampoules are sealed by flaming. In order to avoid solvent evaporation, the mixture can be first frozen in a mixture of dry ice and ethanol prior to flaming the ampoule. The sealed ampoules are then immersed in a water bath at 50° C. for 24 hours.

Preferably, according to the invention, the low molecular weight residual products, such as unreacted monomers, oligomers that were not included in the network and initiator traces are removed from the hydrogel product prior to its use. This may be achieved by immersing the xerogels in ethanol for 20 hours, then in a mixture of ethanol/water (1:1 v/v) for 20 hours and in distilled water for one week with frequent water exchanges until the swelling equilibrium is reached and the rate of extraction is low, preferably zero. Another important aspect of the present invention is to avoid contamination. The preparation of the polymer gel is preferably done in a biohazard chamber with a filtered air flow. The washing steps are preferably performed using sterile materials and the gels are stored at 4° C. in sterile distilled water.

The ploymer mixture can be mixed with living cells, thereby combining the physical characteristics of the polymer matrix with hydrogel-type behavior (porosity, stability, guidance surfaces, permeability) and cellular biological factors (e.g., growth factors).

The introduction of the cells into a polymer matrix is achieved by a gel-entrapment process at a temperature below zero, i.e., cryopolymerization, that yields a porous matrix within which cells are immobilized and can achieve reorganization, growth and/or differentiation for subsequent transplantation. The solvent should be and isotonic solution or tissue culture medium of the type which is commonly used in cell and tissue cultures combined with a suitable cryoprotectant (glycerol/dimethylsufoxide or glycerol or DMSO or polyvinylpyrrolidone or hydroxyethyl starch, carboxymethylcellulose). The process allows to control the final cell densities ranging from a few cells to cell densities approaching the cell density of tissue, approximately $10^9$ to $10^{10}$ cells/cm$^3$. The process allows also to vary and control the matrix porosity by varying the rate of cooling and the temperature of the polymerization mixture containing cells (liquid nitrogen or cooled isopentane). The process yields a macroporous spongy structure typical of cryogel with pore size that permit diffusion of nutrients and macromolecules (e.g., growth factors) to and from the cells entrapped within the polymer gel matrix and cellmigration, and a pore volume suitable for effective biomass accumulation, expansion (cell division) and organization (cell-to-cell contact) during tissue development and maturation.

This approach for fabrication of polymer hydrogel hybrid tissue has two main advantages compared to the procedure disclosed by Woerly et al. (1996): prevention of membrane cell damage by polymerization at low temperature, and the formation of ice crystal around the cells that result in an increased porosity and a fixed pore structure (heterogeneous hydrogel). As a result, the cells are entrapped within the polymeric matrix with a scaffold architecture for organization, large inner surface area, sufficient void spaces for cell expansion and increased permeability. In addition, the cell polymer mixture can be kept stored once frozen for subsequent polymerization as described above.

At any stage of cell development, the resulting hybrid matrix consists of a solid phase that comprises the porous matrix, the cell and the cell extracellular matrix, and a fluid phase corresponding to the cell culture medium and extracellular fluids.

As will be appreciated by one skilled in the art, this process is different from the so-called process "cell encapsulation" that uses micro or macroencapsulation techniques and wherein the cells are simply enclosed within a polymer membrane having a spherical shape of variable diameter.

As used herein, the terms "cells(s)" intend to include tissue fragments, cell clumps, single cells from embryonic, neonatal or adult origin, genetically modified cells, either primary cells or immortalized cells, immortalized cell lines either from existing tumor cell lines or immortalized precursor cell lines, stem or progenitor cells, growth factor-selected precursor cell lines of any tissues and organs. The process and product of this invention are suitable for preparing a wide variety of artificial tissue or organs for transplantation or of three-dimensional culture systems.

To achieve this, for example, a cell suspension in Hank's balanced salt solution (sterile HBSS, pH 7.4) containing 10% to 20% glycerol as cryoprotectant was incubated for 10 minutes at 4° C. The photopolymerization solution consisting of a polymerizable composition as described in EXAMPLE 1 is dissolved in HBSS containing 10% to 20% glycerol. The solution is filtered through a porous glass filter and deaerated in vacuo and precooled in ice. Free radical polymerization is initiated with persulfate ascorbic acid of persulfate tetramethylenediamine dissolved in HBSS. The pH of the solution is adjusted to neutral with HCl 1N. The cells are suspended in the polymerization solution at a variable density, preferably $10^6$ cells/ml of polymerization mixture. The mixture is thoroughly mixed and loaded in a syringe and injected in ampoules or in a mold made of two glass plates separated by silicone rubber sealant of variable sizes or in ampoules. The mold or ampoules are rapidly frozen by immersion in liquid nitrogen and transferred in a water bath cooled at −10° to −30° C. The cryopolymerization reaction is carried out for at least 5 hours, preferably 12 hours. After polymerization, the molds or ampoules are thawed off in a 37° C. water bath and the gels are removed, washed with HBSS, and can be sized to appropriate shapes. The gels are transferred to a 5% $CO_2$ incubator with the preferred culture medium containing antibiotics and antifungic drugs. The procedure is done in a flow cabinet and using sterile instruments.

TEST 1

Figure 4:
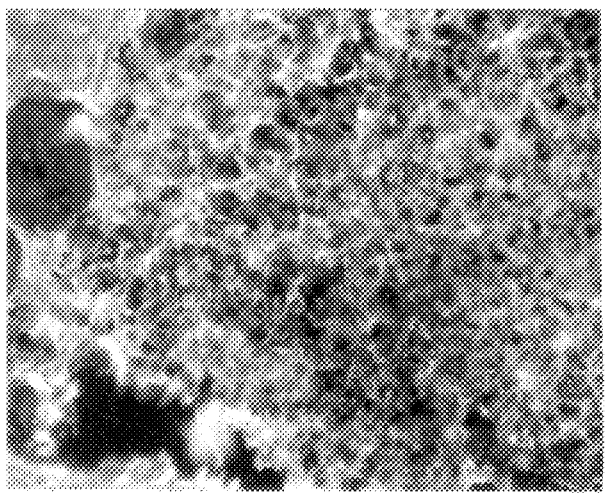
FIG. 4 is a microscopical view of a gel of FIG. 3 implanted in nervous tissue.

The biological tolerance of the polymer hydrogels of the invention was studied by implantation in the transected spinal cord and in brain lesions of rats. Samples for testing were taken up from 1 week up to 10 months after implantation. Biological tolerance was excellent. Macroscopically, the gels integrate to host tissue showing a good stability and in some cases the host organ appears intact. Microscopically, studies have shown that this polymer hydrogel formulation promotes tissue restructuring and axonal regeneration at the site of implantation in the hemi- and transected rat spinal cord and thus achieving up to 100% of tissue continuity restoration (FIG. 4). Data are summarized as follows: (i) integration of the hydrogel and restoration of the continuity of the organ; the hydrogel keeps the volume of lesion constant so that a new tissue can develop and replace the lesion by adhesion of its porous surface to the wound; (ii) smooth interface with the total available polymer surface; (iii) minimal scarring and absence of cystic cavitation in the adjacent host tissue; (iv) ingrowth of a glial-based tissue network within the polymer network reinforcing the attachment of the implant to the host; (v) ingrowth of cells of heterogeneous origin; (vi) capillary ingrowth; (vii) deposition of extracellular matrix molecules (collagen, fibronectin and laminin) at the surface of the polymer network as seen by immunohistochemistry, and (viii) axonal growth throughout the bioimplant. Infrared spectroscopy studies of explanted hydrogels shows that the infrared spectrum of the native hydrogel (non implanted) has been substituted by typical infrared features of lipid and protein compounds similar to the adjacent spinal tissue, confirming that spinal cord tissue elements are integrated to the porour network of the hydrogel.

TEST 2

The cryopolymerisation procedure allowed to generate heterogeneous gels with fixed macroporous structure into which cells are immobilized. Studies using cell labeling technique, such as cell labeling or immunocytochemistry, show that the cells are uniformly distributed throughout the polymer network and at different levels within the gels, either as individual isolated cells or arranged in small clusters of a few cells. The cells which survive were positively immunostained throughout three weeks in vitro incubation with antigenic profiles of developing neural tissue cells. Hence, astrocytes isolated from the neonatal brain of rats can be trapped within hydrophilic hydrogels by cryopolymerization reaction with high levels of retention and the entrapped cells can survive and normally differentiate as they do in monolayer culture conditions: after 10 days in vitro, the viability of entrapped cells is of 90% using cell labeling techniques. In addition, the cells are functional as they synthesize laminin and fibronectin within the polymer matrix as they do in monolayer cultures.

It is understood that the present invention is not limited to the preferred embodiments described above and that modifications are possible without departing from the spirit and scope of the present invention.

I claim:

1. A polymer hydrogel for therapeutic use, comprising:
   a copolymer of (a) and N-substituted methacrylamide or acrylamide, (b) a cross-linking agent and (c) at least one type of copolymerizable, biologically active molecule, which is a complex sugar, a sugar derivative or a tissue adhesive peptide, said polymer hydrogel being heterogeneous, elastically deformable and having an equilibrium water content of at least about 80%, a fractional porosity of at least 80–90%, a mean pore diameter of about 15–35 $\mu$m and a porous volume of pores measuring at least 10 $\mu$m equal to substantially 100% of the total fractional porosity of the hydrogel.

2. The polymer hydrogel of claim 1, wherein (a) said N-substituted methacrylamide or acrylamide is selected from the group consisting of N-monoalkyl and N,N-dialkylmethacrylamides and acrylamides, (b) said cross-linking agent is acrylamide or precursors thereof, and (c) said copolymerizable, biologically active molecule, which is tissue adhesive, is glucosamine, N-acetylglucosamine or an N-acetyl derivative of neuraminic acid.

3. The ploymer hydrogel of claim 2, wherein said alkyl group contains 1–2 carbon atoms.

4. The polymer hydrogel of claim 3, wherein said alkyl is a hydroxyalkyl or an aminoalkyl.

5. The polymer hydrogel of claim 1, wherein said equilibrium water content is at least 96%.

6. The polymer hydrogel of claim 1, wherein said hydrogel is covalently cross-linked and substantially non-transparent.

7. The polymer hydrogel of claim 6, wherein said hydrogel shows a clear phase separated structure formed of polymer particles of about 1–10 $\mu$m, thereby providing an area of relatively coarse porosity where the hydrogel is intended to interface with a host tissue and of relatively fine porosity where it is intended to interface with ingrowing tissue.

8. The polymer hydrogel of claim 1, which has a specific surface area of at least 100 m$^2$/gram and a hyperporous character in the range of 20 to 30 $\mu$m.

9. A method for preparing a heterogeneous, elastically deformable hydrogel for therapeutic use, which comprises:

(a) dissolving a cross-linking agent in a solvent with a free radical polymerization initiator selected from the group consisting of azobisisobutyronitrile, a peroxide, ascorbic acid, a peroxysulfate or a substituted azo compound, said initiator being present in an amount ranging from 0.01–2% by weight with respect to the polymer hydrogel which is formed, to form a solution;

(b) adding an N-substituted methacrylamide or acrylamide to the solution obtained in (a) to form a mixture, (c) adding a solution of a copolymerizable, biologically active molecule, which is a complex sugar, a sugar derivative or a tissue adhesive peptide, to said solution; and (d) polymerizing the components (a) to (c), thereby obtaining a polymer hydrogel which is heterogeneous, elastically deformable and has an equilibrium water content of at least about 80%, a fractional porosity of at least 80–90%, a mean pore diameter of about 15–25 $\mu$m and a porous volume of pores measuring at least 10 $\mu$m equal to substantially 100% of the total fractional porosity of the hydrogel.

10. The method of claim 9, which comprises:

dissolving azobisisobutyronitrile and methylene bisacrylamide in said solvent, thereby forming a solution;

mixing said solution with N-(2-hydroxypropyl) methacrylamide;

adding glucosamine or N-actylglucosamine or N-acetylneuraminic acid thereto;

polymerizing the monomer mixture; and removing low molecular weight residual products and initiator traces therefrom.

11. The method of claim 9, wherein said cross-linking agent is acrylamide, precursors thereof or diving cross-linking agents.

12. The method of claim 9, wherein said complex sugar is glucosamine, N-acetylglucosamine, N-acetyl derivatives of neuraminic acid, polysialic acid or galactosamine derivatives.

13. The method of claim 9, wherein said solution of polymerizable material comprises at least one type of tissue adhesion peptide.

14. The method of claim 9 wherein the copolymerization reaction is conducted at a temperature ranging from 40°–60° C. for about 12 hours.

* * * * *